(12) United States Patent
Lu et al.

(10) Patent No.: US 10,005,958 B2
(45) Date of Patent: Jun. 26, 2018

(54) POLYURETHANE-BASED UV ABSORBER

(71) Applicant: Everlight Chemical Industrial Corporation, Taipei (TW)

(72) Inventors: Mei-Ting Lu, Taoyuan (TW); Huei-Jen Yang, Taoyuan (TW); Yuan-Pin Pan, Taoyuan (TW); Tzu-Heng Ko, Taoyuan (TW); Der-Gun Chou, Taoyuan (TW); Bao-Kun Lai, Taoyuan (TW)

(73) Assignee: EVERLIGHT CHEMICAL INDUSTRIAL CORPORATION, Taipei (TW)

( * ) Notice: Subject to any disclaimer, the term of this patent is extended or adjusted under 35 U.S.C. 154(b) by 0 days. days.

(21) Appl. No.: 15/610,673

(22) Filed: Jun. 1, 2017

(65) Prior Publication Data

US 2018/0002602 A1 Jan. 4, 2018

(30) Foreign Application Priority Data

Jun. 29, 2016 (TW) .............................. 105120500 A

(51) Int. Cl.

| | | |
|---|---|---|
| *C09K 15/30* | (2006.01) |
| *C08G 18/48* | (2006.01) |
| *C08G 18/73* | (2006.01) |
| *C08G 18/34* | (2006.01) |
| *C08G 18/38* | (2006.01) |
| *C08G 18/66* | (2006.01) |
| *C07D 403/14* | (2006.01) |
| *C08G 18/79* | (2006.01) |
| *C08G 18/08* | (2006.01) |
| *C08G 18/10* | (2006.01) |
| *C08G 18/12* | (2006.01) |
| *C08G 18/32* | (2006.01) |
| *D06M 15/564* | (2006.01) |
| *D06N 3/00* | (2006.01) |
| *D06N 3/14* | (2006.01) |

(52) U.S. Cl.
CPC ............ *C09K 15/30* (2013.01); *C07D 403/14* (2013.01); *C08G 18/0809* (2013.01); *C08G 18/0823* (2013.01); *C08G 18/10* (2013.01); *C08G 18/12* (2013.01); *C08G 18/3228* (2013.01); *C08G 18/348* (2013.01); *C08G 18/3851* (2013.01); *C08G 18/48* (2013.01); *C08G 18/4833* (2013.01); *C08G 18/6692* (2013.01); *C08G 18/73* (2013.01); *C08G 18/792* (2013.01); *D06M 15/564* (2013.01); *D06N 3/0059* (2013.01); *D06N 3/14* (2013.01); *D06M 2200/25* (2013.01); *D06N 2203/068* (2013.01); *D06N 2209/1678* (2013.01)

(58) Field of Classification Search
CPC ........ C09K 15/30; C08G 18/48; C08G 18/73; C08G 18/348; C08G 18/3851; C08G 18/6692
USPC ........... 252/588; 427/372.2, 387, 387.9, 391, 427/393; 428/423.1, 423.4, 425.1; 528/73, 74, 76, 85; 548/260, 261; 560/24, 25, 26, 27, 32
See application file for complete search history.

(56) References Cited

U.S. PATENT DOCUMENTS

| | | | |
|---|---|---|---|
| 4,387,194 A | 6/1983 | Ottaviani et al. | |
| 5,321,112 A | 6/1994 | Olson | |
| 5,459,222 A * | 10/1995 | Rodgers ................ | C07C 225/16 427/372.2 |
| 6,252,032 B1 * | 6/2001 | Van Antwerp ..... | C08G 18/3842 522/2 |
| 2004/0132954 A1 | 7/2004 | Malz et al. | |
| 2011/0171890 A1 * | 7/2011 | Nakayama .............. | B24B 37/24 451/526 |
| 2012/0296016 A1 * | 11/2012 | Tanaka ...................... | D01F 6/70 524/91 |
| 2016/0060580 A1 * | 3/2016 | Lu ......................... | C11D 3/3726 510/515 |

* cited by examiner

*Primary Examiner* — Bijan Ahvazi
(74) *Attorney, Agent, or Firm* — Bacon & Thomas, PLLC

(57) ABSTRACT

A polyurethane-based UV absorber, obtained by reacting a UV absorber having a reactive hydrogen with a polyisocyanate and a diol or polyol; wherein the weight average molecular weight of the polyurethane-based UV absorber is in a range of 10,000 to 200,000.

10 Claims, No Drawings

POLYURETHANE-BASED UV ABSORBER

CROSS REFERENCE TO RELATED APPLICATION

This application claims the benefits of the Taiwan Patent Application Serial Number 105120500, filed on Jun. 29, 2016, the subject matter of which is incorporated herein by reference.

BACKGROUND OF THE INVENTION

1. Field of the Invention

The present invention relates to a polyurethane-based UV absorber and, more particularly, to a polyurethane-based UV absorber which can enhance the light fastness and has washing fastness.

2. Description of Related Art

Generally, the dyeing process includes pre-treatment, printing and dyeing, and post-treatment. More specifically, pre-treatment includes: singeing, desizing, scouring, bleaching, mercerizing, and heat setting; printing and dyeing includes: dyeing, printing; and post-treatment includes finishing. To prevent having impact on subsequent dyeing process, the aim of pre-treatment is to remove the natural impurities of yarn or fabric, and substances such as sizing agent, auxiliary, and contaminant. Moreover, the purpose of post-treatment is to enhance the usability or property of fabric (such as color fastness, appearance, touch, anti-shrinkage, crease-proof, anti-static electricity, fire-proof, water repellence, and oil repellence), and the process varies with materials and need of fabric.

Commonly, light fastness enhancer (such as UV absorber and light stabilize) is added in post-treatment to prevent fabric from photo-degradation caused by exposure to sunlight (UV) and maintain the lifespan of fabric. Currently, there are numerous materials, such as solution of zinc oxide (ZnO) and titanium dioxide ($TiO_2$), benzotriazole derivatives, and benzophenone derivatives which are capable of absorbing UV and can be used for treating a textile to enhance light fastness. However, some of those materials only can be used in specific textiles and dyes because of their poor hydrophilicity; some are hydrophilic but lack of great fastness; some have downsides, such as poor fastness and washing fastness; and some are applied with a significant amount of organic solvent or surfactant which is not environment friendly. Especially, the effect of light fastness enhancer decreases dramatically after washing, thus, it has poor washing fastness and shorter lifespan.

Therefore, it is desirable to provide a light fastness enhancer with following advantages: excellent water dispersibility and washing fastness, environment friendly, and can be used in various materials.

SUMMARY OF THE INVENTION

To achieve the object, the present invention provides a polyurethane-based UV absorber so as to provide target objects with excellent washing fastness while enhancing light fastness.

The present invention provides a polyurethane-based UV absorber, obtained by reacting a UV absorber having a reactive hydrogen with a polyisocyanate and a diol or polyol; wherein the weight average molecular weight of the polyurethane-based UV absorber is in a range of 10,000 to 200,000, preferably between 10,000 and 170,000, more preferably between 10,000 and 150,000.

In the present invention, there is no particular limit to the UV absorber, and it merely needs a reactive hydrogen. Preferably, the reactive hydrogen as functional group is selected from a group consisting of —OH, —$NH_2$, and —NH—. More preferably, the UV absorber is selected from the group consisting of benzotriazole UV absorber, benzophenone UV absorber, triazine UV absorber, oxanilide UV absorber, and cyanoacrylate UV absorber. Most preferably, the said UV absorber is a benzotriazole UV absorber.

In the present invention, polyisocyanate can include two or more —NCO functional group, preferably three —NCO functional group. After the reaction between the UV absorber and the polyisocyanate, the reactive hydrogen of UV absorber can be bonded with the —NCO functional group of polyisocyanate. More particularly, said polyisocyanate is selected from a group consisting of isophorone diisocyanate (IPDI), 4,4'-dicyclohexylmethane diisocyanate (HMDI), hexamethylene diisocyanate (HDI), 1,3-Bis(isocyanatomethyl)benzene (XDI), tetramethyl xylylene diisocyanate (TMXDI), hexamethylene diisocyanate trimer (HDI TRIMER), hexamethylene diisocyanate biuret (HDB), and a mixture thereof. Preferably, the polyisocyanate is selected from the group consisting of hexamethylene diisocyanate trimer (HDI TRIMER), Hexamethylene diisocyanate biuret (HDB) and a mixture or polymer thereof.

In the present invention, the diol or polyol can include two or more —OH functional group, therefore, the diol or polyol can be connected to —NCO functional group after the reaction between diol or polyol and polyisocynante is completed. The diol or polyol is selected from the group consisting of anionic diol or polyol, cationic diol or polyol, nonionic diol or polyol, and a mixture thereof. More specifically, the anionic diol or polyol is selected from the group consisting of 2,2-Bis(hydroxymethyl)butyric acid (DMBA), 2,2-Bis(hydroxymethyl)propionic acid (DMPA), 1,4-butanediol-2-Sodium, and a mixture thereof; the cationic diol or polyol is selected from the group consisting of N-methyldiethanolamine (MDEA), methyldiethanolamine (MPEDEA), Triethanolamine, and a mixture thereof; nonionic diol or polyol is selected from the group consisting of ethylene glycol (EG), Diethylene glycol (DEG), 1,4-butanediol (BDO), Polytetramethylene ether glycol (PTMEG), Polyethylene glycol (PEG), Polypropylene glycol (PPG), polyethylene adipate (PEA), polypropylene adipate (PBA), and a mixture thereof. Preferably, the diol or polyol is selected from the group consisting of 2,2-Bis(hydroxymethyl)butyric acid (DMBA), Polyethylene glycol (PEG), N-methyldiethanolamine (MDEA), and a mixture thereof.

In the present invention, the polyurethane-based UV absorber may further include a chain extender. The chain extender is selected from the group consisting of polyamines which comprises two or more reactive hydrogen, and a mixture thereof. The reactive hydrogen as functional group is selected from the group consisting of —OH, —$NH_2$, and —NH—. After the reaction between the chain extender and polyisocyanate is completed, the reactive hydrogen can be connected to the —NCO functional group of polyisocyanate. Specifically, the chain extender is selected from the group consisting of ethyleneamines based polyamines (such as ethylene diamine (EDA), diethylene triamine (DETA), triethylene tetramine (TETA), tetraethylene pentamine (TEPA), pentaethylene hexamine (PEHA), and Aminoethylethanolamine (AEEA)), polyetheramines based polyamines (for example, JEFFAMINE (commercially available from Huntsman)), hydrophilic polyamines (such as aliphatic diamine sulphonate, amino acid, and diaminobenzoic acid), and hydrophobic polyamines (such as 1-amino-3-aminomethyl-3,5,5-trimethylcyclohexane, bis-(4-amino-cyclohexyl)-methane, bis-(4-amino-3-methylcyclohexyl)-methane, 1,6-diaminohexane). Preferably, the chain extender is selected from the group consisting of ethylene diamine (EDA), Aminoethylethanolamine (AEEA), diethylene triamine (DETA), triethylene tetramine (TETA), aliphatic diamine sulphonate, and a mixture thereof. More preferably, the chain extender is selected from the group consisting of ethylene diamine (EDA), aminoethylethanolamine (AEEA), and a mixture thereof.

The structure of the polyurethane-based UV absorber monomer can be represented by formula (I):

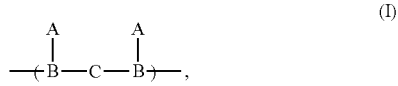

wherein A is UV absorber which includes reactive hydrogen, B is polyisocyanate, and C is diol or polyol.

When the polyurethane-based UV absorber includes the chain extender, the structure of the monomer of polyurethane-based UV absorber can be represented by formula (II):

wherein A, B, and C has the same definition as that defined in the formula (I), and D is chain extender.

The present invention further provides a composition for enhancing light fastness including said polyurethane-based UV absorber, and it can be applied on elastomers, sealants, adhesives, or coatings. Furthermore, the composition for enhancing light fastness may further include an additive which is selected from the group consisting of a neutralizing agent, a carrier, a diluent, an excipient, and a stabilizer.

The said polyurethane-based UV absorber and the composition for enhancing light fastness have excellent adhesiveness to textile, and can be used to treat various materials to enhance light fastness and washing fastness. Therefore, it meets the needs of industry. In addition, said polyurethane-based UV absorber is used without toxic chemicals and additional surfactant, and it is used with extremely low amount of organic solvent, thus, it meets the requirements of environment friendliness.

DETAILED DESCRIPTION OF THE PREFERRED EMBODIMENT

The following specific examples are used to illustrate the present invention. Any person who is skilled in the art can easily conceive other advantages and effects of the present invention. Although the present invention has been explained in relation to its preferred embodiment, many other possible modifications and variations can be made without departing from the spirit and scope of the present invention as hereinafter claimed.

Unless specified otherwise, singular words "a" and "the" used in the invention specification and claims include plural subjects.

Unless specified otherwise, term "or" used in the invention specification and claims include meaning of and/or.

The term "weight average molecular weight" here is Mw value of polystyrene measured by using gel permeation chromatography (GPC) solvent: tetrahydrofuran (THF).

The methods of preparation are described by the following embodiments in details, and the similar methods of embodiments can be used to prepare said polyurethane-based UV absorber. The methods of preparing polyurethane-based UV absorber (such as synthetical method, reaction condition, and sequences) and material are not limited to the present invention.

The polyurethane-based UV absorber has excellent water dispersibility, permeability, and storage stability. Furthermore, it can be widely applied. The polyurethane-based UV absorber can be applied on various materials including, but not limited to, fiber materials, leather materials (such as a natural leather and synthetic leather), foam, and wood. Particularly, the applied fiber materials includes nature fibers (such as plant fibers, animal fibers (for example, wool) and mineral fibers), and artificial fibers (such as regenerated fibers, semi-synthetic fibers, and synthetic fibers (such as polyester fiber and nylon fibers). Preferably, the fiber material is a natural cellulose fiber (such as cotton, linen, flax, hemp, and ramie), an animal fiber (for example, wool), a regenerated fiber (for example, viscose rayon), and a synthetic fiber (such as polyester fibers and nylon fibers). More preferably, the fiber material is cotton. The polyurethane-based UV absorber can be also applied on mixed fibers, blended fabrics or mixed fabrics containing aforementioned fiber materials.

The light fastness enhancer can optionally include other auxiliaries such as, but not limited to, UV absorber, light stabilizer, antioxidant, surfactant, leveling agent, thickener, defoamer and a mixture thereof.

The present invention will be illustrated by preferred embodiment. However, the following examples should not be constructed in any way to limit the scope of the present invention. Unless specified otherwise, percentage referring content and mass used in examples and comparative examples are calculated by weight.

Example 1—Preparation of Compound 1

68.2 g of α-[3-[3-(2H-Benzotriazol-2-yl)-5-(1,1-dimethylethyl)-4-hydroxyphenyl]-1-oxopropyl]-ω-hydroxypoly(oxo-1,2-ethanediyl) (Everlight Chemical Industrial Corporation) was provided in a flask, and then added with 50.5 g of HDI TRIMER. The mixture was then heated to 65-75° C. When the NCO group was titrated till the end point of the reaction (Free NCO %/=7%), 5.4 g of DMBA was added. The mixture is titrated till NCO group was titrated to the end point of the reaction (Free NCO %/=3.99%). Then 16.0 g of acetone and 5.4 g of N,N-Dimethylethylamine were added. Consequently, the prepolymer 1 was obtained.

Prepolymer 1 was added with 300.0 g of deionized water, and then stirred at a high speed. The mixture was added with 2.8 g of EDA and 1.6 g of AEEA as chain extender, and then stirred till dispersed completely. Consequently, the compound 1 (Mw=43,800, measured by GPC) was obtained.

Example 2—Preparation of Compound 2

70.0 g of α-[3-[3-(2H-Benzotriazol-2-yl)-5-(1,1-dimethylethyl)-4-hydroxyphenyl]-1-oxopropyl]-ω-hydroxypoly(oxo-1,2-ethanediyl) (Everlight Chemical Industrial Corporation) was provided in a flask, and then added with 50.5 g HDI TRIMER. The mixture was heated to 65-75° C. When the NCO group was titrated till the end point of the reaction (Free NCO %=6.6%), 2.2 g of DMBA and 10.5 g of PEG300 (polyethylene glycol, Mw=300) were added. Then the NCO group was titrated till the end point of the reaction (Free NCO %=2.8%), and then 16.0 g of acetone and 2.6 g of N,N-Dimethylethylamine were added. Consequently, the prepolymer 2 was obtained.

Prepolymer 2 was added with 300.0 g of deionized water, and then stirred at a high speed. The mixture was added with 2.4 g of EDA and 1.4 g of AEEA as chain extender, and then stirred till dispersed completely. Consequently, the compound 2 (Mw=13,200, measured by GPC) was obtained.

Example 3—Preparation of Compound 3

70.0 g of α-[3-[3-(2H-Benzotriazol-2-yl)-5-(1,1-dimethylethyl)-4-hydroxyphenyl]-1-oxopropyl]-ω-hydroxypoly(oxo-1,2-ethanediyl) (Everlight Chemical Industrial Corporation) was provided in a flask, and then added with 50.5 g HDI TRIMER. The mixture was heated to 65-75° C. When the NCO group was titrated till the end point of the reaction (Free NCO %=7.1%), 1.79 g of MDEA and 10.5 g of PEG300 were added. Then the NCO group was titrated till the end point of the reaction (Free NCO %=3.67%), and then 16.0 g of acetone and 1.8 g of acetic acid were added. Consequently, the prepolymer 3 was obtained.

Prepolymer 3 was added with 300.0 g of deionized water, and then stirred at a high speed till dispersed completely. Consequently, compound 3 (Mw=131,700, measured by GPC) was obtained.

Example 4—Preparation of Compound 4

70.0 g of α-[3-[3-(2H-Benzotriazol-2-yl)-5-(1,1-dimethylethyl)-4-hydroxyphenyl]-1-oxopropyl]-ω-hydroxypoly(oxo-1,2-ethanediyl) (Everlight Chemical Industrial Corporation) was provided in a flask, and then added with 50.5 g HDI TRIMER. The mixture was heated to 65-75° C. When the NCO group was titrated till the end point of the reaction (Free NCO %=6.67%), 3.57 g of MDEA was added. Then the NCO group was titrated till the end point of the reaction (Free NCO %=3.7%), and then 16.0 g of acetone and 4.32 g of acetic acid were added. Consequently, the prepolymer 4 was obtained.

Prepolymer 4 was added with 300.0 g of deionized water, and then stirred at a high speed till dispersed completely. Consequently, the compound 4 (Mw=74,400 measured by GPC) was obtained.

Example 5—Preparation of Compound 5

70.0 g of α-[3-[3-(2H-Benzotriazol-2-yl)-5-(1,1-dimethylethyl)-4-hydroxyphenyl]-1-oxopropyl]-ω-hydroxypoly(oxo-1,2-ethanediyl) (Everlight Chemical Industrial Corporation) was provided in a flask, and then added with 47.8 g HDB. The mixture was heated to 65-75° C. When the NCO group was titrated till the end point of the reaction (Free NCO %=7.2%), 2.2 g of DMBA and 10.5 g of PEG300 were added. Then the NCO group was titrated till the end point of the reaction (Free NCO %=3.5%), 16.0 g of acetone and 2.6 g of N-Dimethylethylamine were added. Consequently, the prepolymer 5 was obtained.

Prepolymer 5 was added with 300.0 g of deionized water, and then stirred at a high speed till dispersed completely. Consequently, the compound 5 (Mw=91,900 measured by GPC) was obtained.

The aforementioned monomer structure of compound 1 and compound 2 can be represented by formula (II), and compound 3 to 5 can be represented by formula (I):

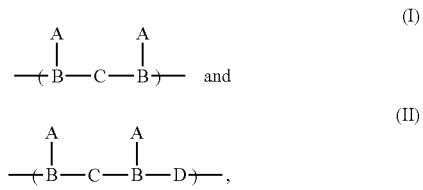

wherein the average weight molecular weight (Mw) of A, B, C, D, and other compounds are shown in Table 1.

TABLE 1

|   | Compound 1 | Compound 2 | Compound 3 | Compound 4 | Compound 5 |
|---|---|---|---|---|---|
| A | UVA | UVA | UVA | UVA | UVA |
| B | HDI TRIMER | HDI TRIMER | HDI TRIMER | HDI TRIMER | HDB |
| C | DMBA | DMBA/PEG300 | MDEA/PEG300 | MDEA | DMBA/PEG300 |
| D | EDA/AEEA | EDA/AEEA | — | — | — |
| Mw | 43,800 | 13,200 | 131,700 | 74,400 | 91,900 |

UVA is UV absorber, which is α-[3-[3-(2H-Benzotriazol-2-yl)-5-(1,1-dimethylethyl)-4-hydroxyphenyl]-1-oxopropyl]-ω-hydroxypoly(oxo-1,2-ethanediyl).

Comparative Example 1

55.67 g of α-[3-[3-(2H-Benzotriazol-2-yl)-5-(1,1-dimethylethyl)-4-hydroxyphenyl]-1-oxopropyl]-ω-hydroxypoly(oxo-1,2-ethanediyl) (Everlight Chemical Industrial Corporation) was provided in a 250 ml flask, and then stirred. Then heated to 50° C., and then added with 22.20 g of HDI TRIMER and 19.50 g of DMAc (N,N-Dimethylacetamide). The mixture was heated to 90° C., and the reaction was performed for 2-3 hours (the NCO group was titrated till the end point of the reaction). Then, the mixture was cooled down to 70° C., and then added with 2.59 g of MDEA (N-methyldiethanolamine), which is neutralized by 1.30 g of AcOH (acetic acid) in advance, and 7.20 g of DMAc. The mixture was heated to 90° C., and the reaction was performed for 2-3 hours (the NCO group was titrated till the end point of the reaction). The mixture was cooled down to 50° C., and then the comparative example 1 was obtained.

The aforementioned monomer structure of comparative example 1 can be represented by formula (I):

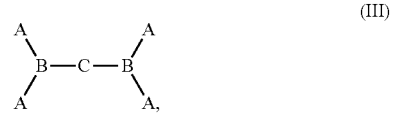

wherein A is α-[3-[3-(2H-Benzotriazol-2-yl)-5-(1,1-dimethylethyl)-4-hydroxyphenyl]-1-oxopropyl]-ω-hydroxypoly(oxo-1,2-ethanediyl), B is HDI TRIMER, and C is MDEA. The average weight molecular weight of comparative example 1 is about 3608.4.

Test Example 1—Light Fastness Test

The solution (80 g/l-120 g/l) of aforementioned examples and comparative examples were poured over the roller of a padding machine to proceed padding treatment for dyed sample fabrics (13 cm×5 cm) under less than 80% of wet pickup condition, and then dyed sample fabrics were put in an oven at 60° C. for 15 minutes. After drying, dyed sample fabrics were divided into two groups which are non-washed group and washed-five-times group. Non-washed group was conducted light fastness testing according to AATCC 16-2010 method 3 (20 light units), and measured the degree of fading by a spectrophotometer after exposure to artificial daylight. The results were graded by the instrument. Furthermore, the washed five-times-group was conducted a light fastness testing after washing testing as follows.

Test Example 2—Washing Test

The washed five-times-group was provided, and added with the accompanying fabric, which is 50/50 poly-cotton blend (92 cm×92 cm), to 1.8 kg in total. Then added with 66 g of washing powder (1933 AATCC washing powder) to wash, and the water temperature was set as 49° C.±3° C. The washing procedure was set as standard setting: water level is 18±0.5 gal; agitation speed is 179±$^2$ spm; washing time is 12 minutes; spin speed is 645±15 rpm; final spin time is 6 minutes. The dyed sample fabrics were added with 66 g of washing powder to proceed next washing cycle without drying until 5 washing cycles were finished. The washing procedure is conducted according to AATCC 135-2004' method.

The results of non-washed group and washed five-times-group are shown in table 2 and table 3 respectively. The Blank is dyed sample fabrics without adding any solution.

TABLE 2

| | Comparative example 1 | Compound 1 | Compound 2 | Compound 3 | Compound 4 | Compound 5 |
| --- | --- | --- | --- | --- | --- | --- |
| Blank | Grade: 3 | Grade: 3.5 | Grade: 3 | Grade: 2.5 | Grade: 2.5 | Grade: 2.5 |
| Non-washed | Grade: 4 | Grade: 4.5 | Grade: 4 | Grade: 3.5 | Grade: 3.5 | Grade: 3.5 |
| Enhanced grade of light fastness | 1 | 1 | 1 | 1 | 1 | 1 |

TABLE 3

| | Comparative example 1 | Compound 1 | Compound 2 | Compound 3 | Compound 4 | Compound 5 |
| --- | --- | --- | --- | --- | --- | --- |
| Blank | Grade: 3 | Grade: 3.5 | Grade: 3 | Grade: 2.5 | Grade: 2.5 | Grade: 2.5 |
| Washed five times | Grade: 3 | Grade: 4 | Grade: 4 | Grade: 3 | Grade: 3.5 | Grade: 3.5 |
| Enhanced grade of light fastness | 0 | 0.5 | 1 | 0.5 | 1 | 1 |

It can be seen that light fastness of dyed sample fabrics was enhanced by 1 grade after added with solution of compounds according to table 2. In accordance with table 3, the light fastness of dyed sample fabrics added with comparative example 1 solution decreased after washing five times. By contrast, the light fastness of dyed sample fabrics added with solution of examples 1-5 were still enhanced by 0.5-1 degree. Further, examples 1 and 2 comprise chain extender respectively and examples 3-5 do not comprise chain extender; by comparison, both of them provide dyed sample fabrics with excellent light fastness and washing fastness.

Although the present invention has been explained in relation to its preferred embodiment, it is to be understood that many other possible modifications and variations can be made without departing from the spirit and scope of the invention as hereinafter claimed.

What is claimed is:

1. A polyurethane-based UV absorber, obtained by reacting a UV absorber having a reactive hydrogen with a polyisocyanate and a diol or polyol; wherein the UV absorber is α-[3-[3-(2H-Benzotriazol-2-yl)-5-(1,1-dimethylethyl)-4-hydroxyphenyl]-1-oxopropyl]-ω-hydroxypoly(oxo-1,2-ethanediyl), the polyisocyanate is hexamethylene diisocyanate trimer (HDI TRIMER) or hexamethylene diisocyanate biuret (HDB), and the weight average molecular weight of the polyurethane-based UV absorber is in a range of 10,000 to 200,000.

2. The polyurethane-based UV absorber according to claim 1, wherein the diol or polyol is selected from the group consisting of anionic diol or polyol, cationic diol or polyol, nonionic diol or polyol, and a mixture thereof.

3. The polyurethane-based UV absorber according to claim 2, wherein the anionic diol or polyol is selected from the group consisting of 2,2-Bis(hydroxymethyl)butyric acid (DMBA), 2,2-Bis(hydroxymethyl)propionic acid (DMPA), 1,4-butanediol-2-Sodium, and a mixture thereof.

4. The polyurethane-based UV absorber according to claim 2, wherein the cationic diol or polyol is selected from the group of N-methyldiethanolamine (MDEA), methyldiethanolamine (MPEDEA), Triethanolamine, and a mixture thereof.

5. The polyurethane-based UV absorber according to claim 2, wherein the nonionic diol or polyol is selected from the group consisting of ethylene glycol(EG), diethylene glycol (DEG), 1,4-butanediol (BDO), polytetramethylene ether glycol (PTMG), polyethylene glycol (PEG), polypropylene glycol (PPG), polyethylene adipate (PEA), polypropylene adipate (PBA), and a mixture thereof.

6. The polyurethane-based UV absorber according to claim 1, wherein a chain extender is further reacted with the polyisocyanate and the diol or polyol.

7. The polyurethane-based UV absorber according to claim 6, wherein the chain extender is selected from the group consisting of polyamines, which comprises two or more reactive hydrogen as functional group selected from the group consisting of —OH, —NH$_2$, and —NH—, and a mixture thereof.

8. A composition for enhancing light fastness, comprising the polyurethane-based UV absorber according to claim 1.

9. The composition according to claim 8, further comprising an additive which is selected from the group consisting of a neutralizing agent, a carrier, a diluent, an excipient, and a stabilizer.

10. The composition according to claim 8, which is applied on coatings, adhesives, sealants, or elastomers.

* * * * *